United States Patent
Bales et al.

(10) Patent No.: US 11,110,186 B2
(45) Date of Patent: Sep. 7, 2021

(54) ANIONIC CHELATE COMPOUNDS

(71) Applicant: GENERAL ELECTRIC COMPANY, Schenectady, NY (US)

(72) Inventors: Brian Christopher Bales, Niskayuna, NY (US); Michael James Rishel, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/956,995

(22) PCT Filed: Dec. 20, 2018

(86) PCT No.: PCT/EP2018/086426
§ 371 (c)(1),
(2) Date: Jun. 22, 2020

(87) PCT Pub. No.: WO2019/122255
PCT Pub. Date: Jun. 27, 2019

(65) Prior Publication Data
US 2020/0338217 A1 Oct. 29, 2020

Related U.S. Application Data

(60) Provisional application No. 62/608,387, filed on Dec. 20, 2017.

(51) Int. Cl.
*A61K 49/10* (2006.01)
*C07F 13/00* (2006.01)

(52) U.S. Cl.
CPC .......... *A61K 49/106* (2013.01); *C07F 13/005* (2013.01)

(58) Field of Classification Search
CPC ... A61K 49/106; C07B 59/004; C07D 471/08
See application file for complete search history.

(56) References Cited

U.S. PATENT DOCUMENTS

| 5,876,695 A | 3/1999 | Gries et al. |
| 2016/0101196 A1 | 4/2016 | Medina et al. |

FOREIGN PATENT DOCUMENTS

| EP | 0258616 A1 | 7/1987 |
| EP | 0463644 A2 | 1/1992 |
| EP | 2457914 A1 | 5/2012 |
| EP | 2988756 B1 | 8/2017 |
| WO | 2009103744 A2 | 8/2009 |
| WO | 2011073371 A1 | 6/2011 |
| WO | 2017220610 A1 | 12/2017 |
| WO | 2018115314 A1 | 6/2018 |

OTHER PUBLICATIONS

Drahoš, et al., "Manganese (II) Complexes as Potential Contrast Agents for MRI," EurJIC, European Journal of Inorganic Chemistry, Microreview, [no date] 2012, pp. 1975-1986.

Henig, et al., "Macrocyclic Gd3+ Chelates Attached to a Silsesquioxane Core as Potential Magnetic Resonance Imaging Contrast Agents: Synthesis, Physicochemical Characterization, and Stability Studies," Inorganic Chemistry Article, 49, pp. 6124-6138.

Kubiček, et al., "Design and Function of Metal Complexes as Contrast Agents in MRI," Centre de Biophysique Moleculaire, France, Advance in Inorganic Chemistry, vol. 61 ISSN 08998-8838, [no date] 2009, 67 pages.

Sieber, et al. "Gadolinium-Based Contrast Agents and Their Potential Role in the Parthenogenesis of Nephrogenic Systemic Fibrosis: The Role of Excess Ligand," Journal of magnetic Resonance Imaging 27:955-962, [no date] 2008, 8 pages.

Notification of Transmittal of the International Search Report and the Written Opnion of the International Searching Authority, or the Declaration of International Application No. PCT/EP2018/086426, dated Mar. 15, 2019, 11 pages.

*Primary Examiner* — Michael G. Hartley
*Assistant Examiner* — Leah H Schlientz
(74) *Attorney, Agent, or Firm* — Jeff B. Vockrodt; Culhane Meadows, PLLC

(57) ABSTRACT

The invention provides compounds suitable for use as contrast agents in magnetic resonance imaging (MRI). The compounds of the present invention are manganese (II) complexes having advantageous properties as compared with similar known compounds.

14 Claims, 2 Drawing Sheets

ANIONIC CHELATE COMPOUNDS

TECHNICAL FIELD OF THE INVENTION

The invention relates to chelate compounds and their use as contrast agents in magnetic resonance procedures.

DESCRIPTION OF RELATED ART

Magnetic resonance imaging (MRI) is a medical imaging technique in which areas of the body are visualised via the nuclei of selected atoms, especially hydrogen nuclei. The MRI signal depends upon the environment surrounding the visualised nuclei and their longitudinal and transverse relaxation times, respectively referred to as T1 and T2. Thus, in the case when the visualised nucleus is a proton, the MRI signal intensity will depend upon factors such as proton density and the chemical environment of the protons.

Contrast agents that include a paramagnetic metal ion in their chemical structure can be used in MRI to improve the imaging contrast. They work by influencing the relaxation times and consequently the contrast in the images. Contrast agents comprising the paramagnetic metal ion Gd(III) are well known, and include the commercially-available Gd(III) chelates Omnisca™ (GE Healthcare), Dotarem™ (Guerbet), Gadavist™ (Bayer) and Magnevist™ (Bayer). Because of their low molecular weight they rapidly distribute into the extracellular space (i.e. the blood and the interstitium) when administered into the vasculature. They are also cleared relatively rapidly from the body. However, not all Gd(III) remains complexed within the chelate in vivo and it is known that free Gd(III) ion can interfere with biological pathways and induce toxicity.

The manganese(II) ion is a paramagnetic species with a high spin number and a long electronic relaxation time and the potential of a Mn(II) based high relaxivity contrast agent has been reported in the literature (Tóth, E; Advances in Inorganic Chemistry, 2009, 61(09), 63-129). Mn(II) has also been suggested as a less toxic alternative to Gd(III). However, known Mn(II) chelates have proved to be much less stable compared to corresponding Gd(III) chelates. For example, the Mn(II) chelate of DOTA (MnDOTA) is several hundred times less stable compared to the corresponding Gd(III) complex (GdDOTA (Drahoš, B; Inorganic Chemistry, 2012(12), 1975-1986).

An important problem to be solved is thus that of obtaining novel manganese chelates exhibiting a high stability while maintaining efficacious relaxation properties.

Certain relatively stable manganese chelates are described in WO2011073371. The molecular design described therein has been demonstrated to favour high chelate stability and a high relaxivity. This makes these compounds very suitable for use as MRI contrast agents. An exemplary compound of WO2011073371 has the following structure (referred to hereunder as "Mn Platform"):

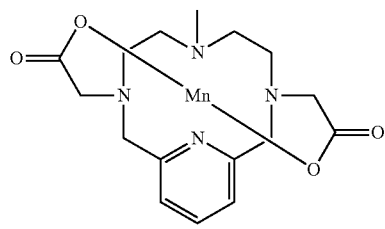

However, there is still scope for improved Mn(II) chelates.

SUMMARY OF THE INVENTION

In one aspect the present invention relates to a compound of Formula I or a salt or solvate thereof:

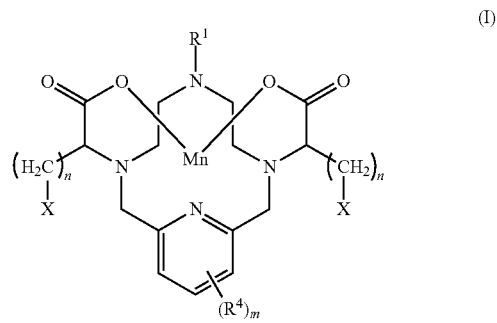

wherein:
n is an integer of 1 to 4
$R^1$ is $C_{1-3}$ alkyl or $-(CH_2)_{n+1}-C(=O)-NR^2R^3$;
each X is $-C(=O)-NR^2R^3$ or $-NH-C(=O)-R^3$;
each $R^2$ is hydrogen, $C_{1-4}$ alkyl or an anionic substituent;
each $R^3$ is an anionic substituent optionally linked via a $C_{1-4}$ alkylene; and,
$R^4$ is independently selected from the group comprising hydroxy, halo, amino, amido, $C_{1-6}$ alkyl and $C_{1-6}$ hydroxyalkyl and m is between 0-3.

In another aspect the present invention relates to a pharmaceutical composition comprising the compound of Formula I as defined herein together with a biocompatible carrier in a form suitable for mammalian administration.

In a further aspect the present invention provides a method comprising:
(i) administration to a subject of the compound of Formula I or the pharmaceutical composition as defined herein;
(ii) detection of magnetic resonance (MR) signals from said subject or part of said subject in which said compound has distributed;
(iii) generation of MR images and/or MR spectra from said detected signals.

In a yet further aspect the present invention provides a method to produce a compound of Formula I as defined herein comprising reaction of a compound of Formula II with a suitable source of manganese:

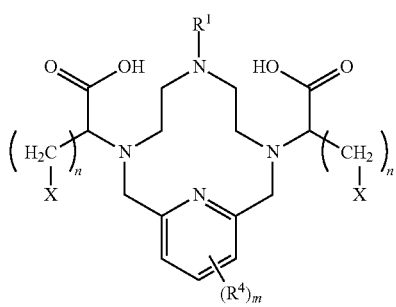

wherein each of X, R$^1$, R$^4$, m and n are as variously defined for Formula I herein.

This invention describes a number of Mn chelate structures useful as MRI contrast agents that maintain a negative charge at physiological pH The Mn chelates of the present invention present a potential alternative to existing Gd agents and may provide a significantly improved safety profile. By using an endogenous metal ion, it is predicted that significant improvements can be achieved in patient safety while at the same time maintaining strong MR contrast in tissue.

The negatively charged Mn chelates of the present invention may also provide an altered clearance profile compared to their neutral counterparts.

DETAILED DESCRIPTION OF THE PREFERRED EMBODIMENTS

Figure 1:
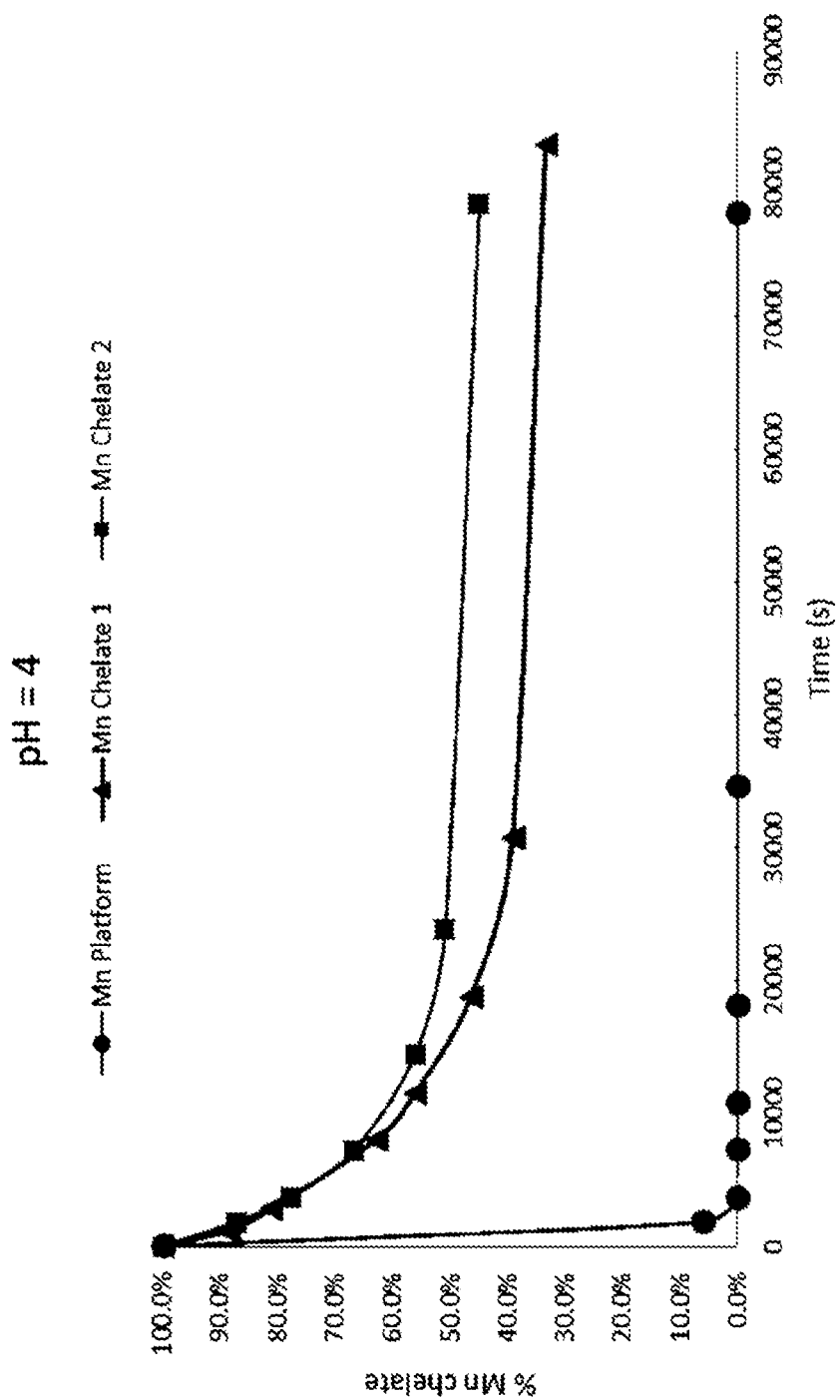
FIG. 1 shows (circles=Mn Platform, triangles=Mn Chelate 1 and squares=Mn Chelate 2) % Mn chelate as a function of time at pH=4 and 40° C. in the presence of 100 fold excess ZnCl$_2$.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

A "salt" according to the invention, include physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids.

A suitable "solvate" according to the invention is selected from ethanol, water, saline, physiological buffer and glycol.

The term "alkyl", alone or in combination, means a straight-chain or branched-chain alkyl radical having the general formula C$_n$H$_{2n+1}$. Examples of such radicals include methyl, ethyl, and isopropyl.

The term "anionic substituent" herein refers to a monovalent radical having a pKa of less than 8. Such substituents are common general knowledge to the person skilled in the art. The term "pKa" takes its normal meaning in the art, i.e. refers to the acid dissociation constant (also known as acidity constant, or acid-ionization constant) and is a quantitative measure of the strength of an acid in solution. For examples of suitable anionic substituents having a pKa less than 8 the reader is referred to the Bordwell pKa table at this link: http://www.chem.wisc.edu/areas/reich/pkatable/.

The term "hydroxy" refers to the group —OH.

The term "halogen" or "halo-" means a substituent selected from fluorine, chlorine, bromine or iodine.

The term "amino" herein refers to the group —NR'R" wherein R' and R" are independently hydrogen or an alkyl.

The term "amido" refers to the group —C(O)NR'R" wherein R' and R" are independently hydrogen or an alkyl.

The term "hydroxyalkyl" refers to an alkyl group as defined herein comprising a hydroxyl substituent.

In one embodiment of the compound of Formula I R$^1$ is C$_{1-3}$ alkyl.

In one embodiment of the compound of Formula I R$^1$ is methyl.

In one embodiment of the compound of Formula I R$^1$ is ethyl.

In one embodiment of the compound of Formula I R$^1$ is —(CH$_2$)$_{n+1}$—C(=O)—NR$^2$R$^3$ wherein n, R$^2$ and R$^3$ are as defined in claim 1.

In one embodiment of the compound of Formula I n is 1.
In one embodiment of the compound of Formula I n is 2.
In one embodiment of the compound of Formula I n is 3.
In one embodiment of the compound of Formula I n is 4.
In one embodiment of compound of Formula I each X is —C(=O)—NR$^2$R$^3$.

In one embodiment of compound of Formula I each each X is —NH—C(=O)—R$^3$.

In one embodiment of the compound of Formula I each anionic substituent comprises a group selected from carboxylate, sulfonate, phosphate and phosphonate.

In one embodiment of the compound of Formula I each anionic substituent comprises carboxylate.

In one embodiment of the compound of Formula I said carboxylate is linked to the amide nitrogen via —CH$_2$—.

In one embodiment of the compound of Formula I each anionic substituent comprises sulfonate. In one embodiment of the compound of Formula I said sulfonate is linked to the amide nitrogen via —CH$_2$—CH$_2$—.

In one embodiment of the compound of Formula I each anionic substituent is tetrazole, thiazolidindione, nitromethylsulfonylphenyl, 4-nitrothiophenol, nitromethylcarboxyphenyl, 2,4-dinitrophenol, or malonitrile.

In some embodiments of the compound of Formula I each anionic substituent is the same.

In some embodiments of the compound of Formula I each R$^2$ is the same.

In some embodiments of the compound of Formula I each R$^3$ is the same.

In some embodiments of the compound of Formula I each X is the same. In one embodiment of the compound of Formula I m is 0.

In one embodiment of the compound of Formula I each anionic substituent has a pKa less than physiological pH.

In one embodiment of the compound of Formula I each anionic substituent has a pKa of less than about 7.5.

In one embodiment of the compound of Formula I each anionic substituent has a pKa of less than about 6.0.

In one embodiment of the compound of Formula I each of said anionic substituents is over 90% anionic at physiological pH.

In one embodiment the compound of Formula I is either a racemic mixture or diastereomerically pure.

In one embodiment the compound of Formula I is diastereomerically pure.

The term "carboxylate" refers to the substituent —COO$^-$.
The term "sulfonate" refers to the substituent —SO$_3^-$.
The term "phosphate" refers to the substituent PO$_4^{3-}$ The term "phosphonate" refers to the substituent —PO(OH)$_2$.

The term "tetrazole" refers to a 5-member ring of four nitrogen atoms and one carbon atom of formula CH$_2$N$_4$.

The term "thiazolidindione" refers to the following heterocyclic substituent:

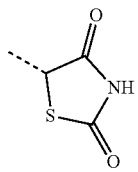

The term "nitromethvlsulfonvlphenvl" refers to the following substituent:

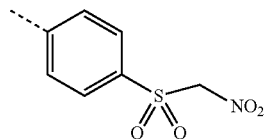

The term "4-nitrothiophenol" refers to the following substituent:

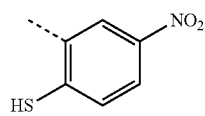

The term "nitromethylcarboxyphenyl" refers to the following substituent:

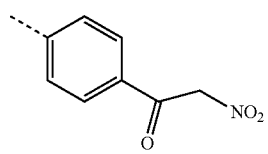

The term "2,4-dinitrophenol" refers to the following substituent:

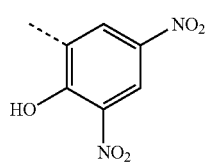

The term "malonitrile" refers to the following substituent:

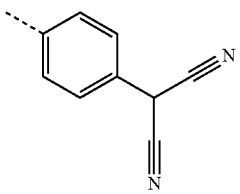

An equimolar mixture of a pair of enantiomers is referred to herein as a "racemic mixture".

The term "enantiomer" refers to an enantiopure compound, i.e. one of the two mirror-image forms of an optically active molecule. An enantiomer is therefore a compound having only one chirality, wherein the term "chirality" refers to that property of a compound whereby it lacks an internal plane of symmetry and has a non-superimposable mirror image. The feature that is most often the cause of chirality in chemical compounds is the presence of an asymmetric carbon atom.

The term "diastereomerically pure" refers to where the compound comprises one enantiomer.

In certain embodiments of the present invention each group (also referred to herein as an "arm") —C(=O)—N—R$^2$R$^3$ of Formula I (i.e. as in Formula I per se or when part of R$^1$ when it is —(CH$_2$)$_{n+1}$—C(=O)—NR$^2$R$^3$) may be selected from the following:

| Structure | pKa (approx.) |
|---|---|
| thiazolidindione | 6.8 |
| nitromethylsulfonylphenyl | 7.1 |
| 4-nitrothiophenol | 5.5 |
| nitromethylcarboxyphenyl | 7.7 |

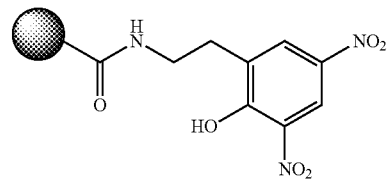

2,4-dinitrophenol
5.1

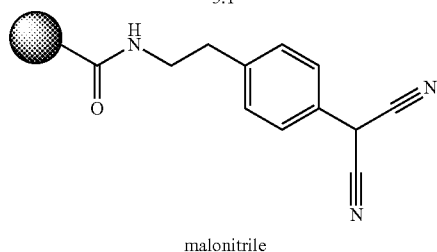

malonitrile

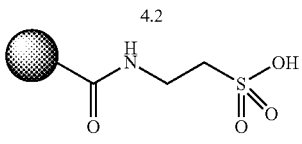

sulfonyl
1.6

= Chelate

It should be noted that the pKa values in the above table are estimated in DMSO. It will be appreciated by the skilled person that the pKa values in water are expected to be lower on the basis that water will be a better solvent for ions.

In certain embodiments the compound of Formula I comprises 2 of the above arms (i.e. wherein $R^1$ is $C_{1-3}$ alkyl). An exemplary such compound is as follows:

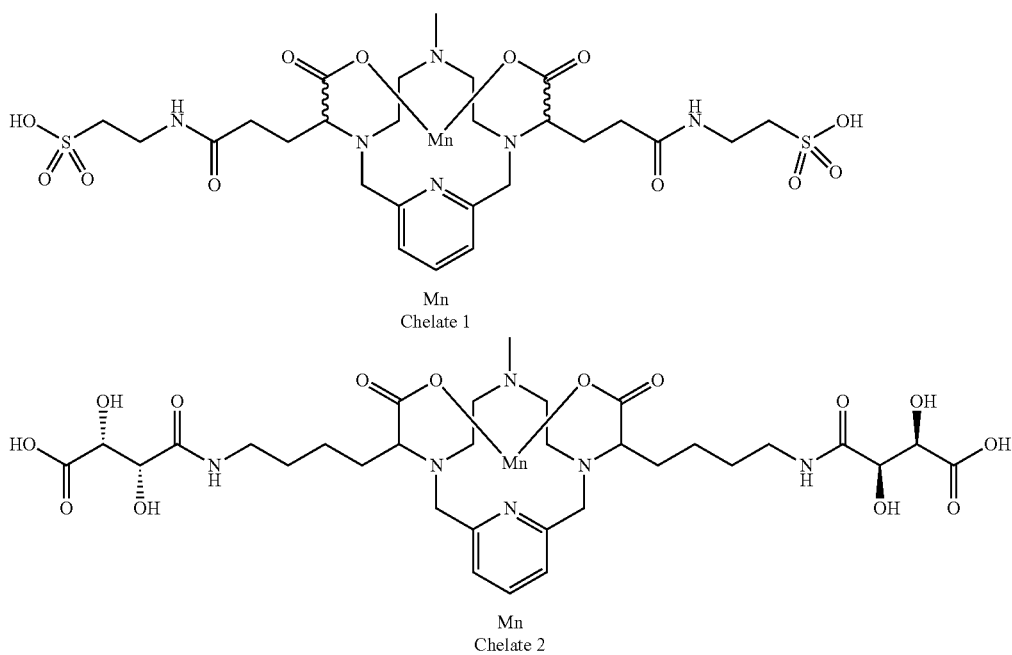

Mn Chelate 1

Mn Chelate 2

In other embodiments the compound of Formula I comprises 3 of the above arms (i.e. wherein $R^1$ is $-(CH_2)_{n+1}-C(=O)-NR^2R^3$).

The following generalized procedure may be used and/or readily adapted using methods well-known to those of skill in the art to obtain compounds of Formula

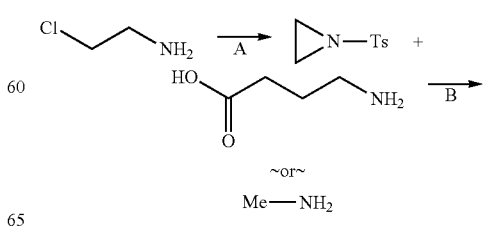

~or~

Me—NH$_2$

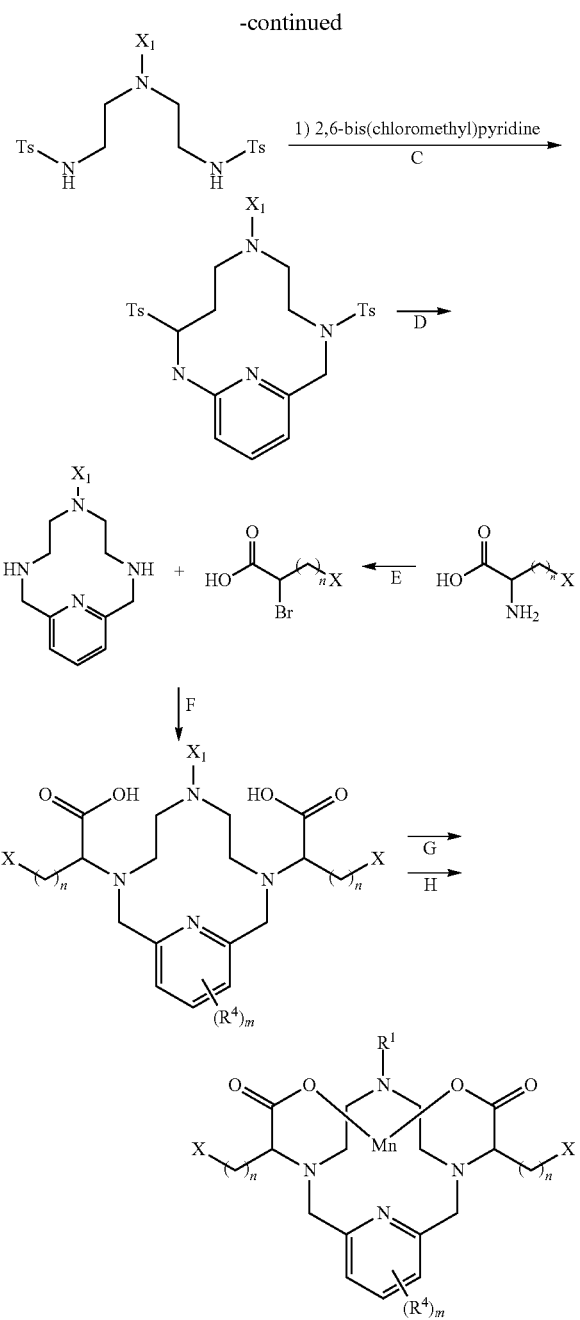

In the above scheme $X^1$ is $CH^3$, a 4-carbon ester, a nitrile or $CH_2CH_2CH_2COOH$ and X, $R^{1-4}$m and n are as defined for Formula I herein.

In summary:

A: Tosylation of 2-chloroethylamine gives aziridine (Carrillo, Arkivoc, 2007).

B: Aziridation of aminobutanoic acid (Sigma Aldrich catalogue 56-12-2). In one embodiment aziridination of methylamine proceeds in neat acetonitrile). In one embodiment for this amino acid some base is used to activate amine.

Optionally the acid functionality could be protected as an ester, nitrile or other carboxylate equivalent.

C: Cyclization with an activated pyridine such as 2,6-bis(chloromethyl)pyridine (Sigma Aldrich catalogue 3099-28-3). In one embodiment, this step is carried out in acetonitrile with potassium carbonate as the base.

D: De-tosylation using in one embodiment concentrated sulphuric acid. In one embodiment, this step proceeds quantitatively.

E: Bromination based on method described in literature (Henig, J., Tóth, É., Engelmann, J., Gottschalk, S., & Mayer, H. a. (2010). Inorganic Chemistry, 49(13), 6124-38).

F: Alkylation of the polyamine. In one embodiment, this step is carried out in aqueous solution. In another embodiment, where secondary halides react sluggishly (primary alkylhalides proceeds well) it is possible to synthesize bis-ester (E) and switch to organic solvent to improve reaction speed.

G: Complexation using MnCl2. Precipitate excess Mn using base.

H: Activate carboxylates with peptide reagents. In one embodiment, these reagents are EDCI and/or HOBT (as described in EP2457914 B1). Couple with suitable amine to result in the desired compound of Formula I. Alternatively, free terminal amines can be coupled with acid chlorides or activated carboxylates.

The compounds of Formula I of the present invention find use as in vivo contrast agents, e.g. for indications similar to current commercially-available gadolinium-based chelate contrast agents. For this application they are suitably administered to a subject as a pharmaceutical composition, which itself forms a further aspect of the present invention.

A "pharmaceutical composition" is a formulation comprising the compound of the invention, together with a biocompatible carrier in a form suitable for mammalian administration. The "biocompatible carrier" is a fluid, especially a liquid, in which the compound of Formula I is suspended or dissolved, such that the resulting composition is physiologically tolerable, i.e. can be administered to the mammalian body without toxicity or undue discomfort (which can be understood to be a definition of the term "suitable for mammalian administration").

The pharmaceutical composition of the invention is suitable for use as a magnetic resonance (MR) contrast medium in magnetic resonance imaging (MRI) of the human and non-human animal body.

In one embodiment, the pharmaceutical composition of the invention may comprise one or more pharmaceutically-acceptable excipients. These suitably do not interfere with the manufacture, storage or use of the final composition.

Non-limiting examples of suitable pharmaceutically-acceptable excipients include buffering agents, stabilizers, antioxidants, osmolality adjusting agents, pH adjusting agents, excess cheland and weak complexes of physiologically tolerable ions. These and other suitable excipients will be well known to those of skill in the art and are further described in e.g. WO1990003804, EP0463644-A, EP0258616-A and U.S. Pat. No. 5,876,695 the content of which are incorporated herein by reference. The pharmaceutical composition of the invention in one embodiment is in a form suitable for parenteral administration, for example injection. The pharmaceutical composition according to the invention may therefore be formulated for administration using physiologically acceptable excipients in a manner fully within the skill of the art. For example, the compound of Formula I, optionally with the addition of pharmaceutically acceptable excipients, may be suspended or dissolved in an aqueous medium, with the resulting solution or suspension then being sterilized.

A non-limiting example of a suitable buffering agent is tromethamine hydrochloride.

The term "excess cheland" is defined as any compound capable of scavenging free paramagnetic ion (manganese), but not paramagnetic ion (manganese) retained within the complexes of this invention, as described in EP2988756A1. Although small amounts are essential to human health, overexposure to free manganese ions may result in the neurodegenerative disorder known as "manganism" with symptoms resembling Parkinson's disease. However, the fundamental issue for Mn, as well as other metals, as contrast agents is in their chelation stability. Chelation stability is an important property that reflects the potential release of free metal ions in vivo. It is known that there is a correlation between the amount of excess cheland in a paramagnetic chelate formulation and the amount of paramagnetic metal deposited in animal models (Sieber 2008 J Mag Res Imaging; 27(5): 955-62). Therefore, in another embodiment, an amount of excess cheland is selected that can act as a Mn scavenger to reduce or prevent release of Mn from the formulation post injection. The optimal amount of free cheland will result in a pharmaceutical composition having suitable physicochemical properties (i.e. viscosity, solubility and osmolality) and avoiding toxological effects such as zinc depletion in the case of too much free cheland. U.S. Pat. No. 5,876,695 describes in particular an excess of linear chelate, in particular of free DTPA, and this is a non-limiting example of an excess cheland suitable for use in the pharmaceutical composition of the present invention. This formulation strategy is used for products such as Magnevist™, Vasovist™ or Primovist™. WO2009103744 describes a similar formulation strategy, based on the addition of a precise amount of free chelate, to have a very small excess of said chelate and a zero concentration of free lanthanide.

The physiologically tolerable ion may in one embodiment be selected from physiologically tolerable ions include calcium or sodium salts such as calcium chloride, calcium ascorbate, calcium gluconate or calcium lactate.

Parenterally administrable forms should be sterile and free from physiologically unacceptable agents and should have low osmolality to minimize irritation or other adverse effects upon administration and thus the pharmaceutical composition should be isotonic or slightly hypertonic. Non-limiting examples of suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 22$^{nd}$ Edition (2006 Lippincott Williams & Wilkins) and The National Formulary (https://books.google.com/books?id=O3qixPEMwssC&g=THE+NATIONAL+FORMULARY*dg=THE+NATIONAL+FORMULARY&hl=en&sa=X&ved=0CC8Q6AEwAGoFChMlmfPHrdTgyAlVJfNyCh1RJw_E).

For the pharmaceutical composition of the invention to be administered parenterally, i.e. by injection its preparation further comprises steps including removal of organic solvent, addition of a biocompatible buffer and any optional further ingredients such as excipients or buffers. For parenteral administration, steps to ensure that the pharmaceutical composition is sterile and apyrogenic also need to be taken.

In another aspect, the present invention provides a method comprising administration of the compound of Formula I as defined herein in the generation of MR images and/or MR spectra.

Methods of administration and subjects envisaged as suitable in the context of the present invention have been described hereinabove in connection with the pharmaceutical composition. Administration of the compound of Formula I is preferably carried out parenterally, and most preferably intravenously. The intravenous route represents the most efficient way to deliver the compound throughout the body of the subject. Furthermore, intravenous administration does not represent a substantial physical intervention or a substantial health risk. The compound of Formula I of the invention is preferably administered as the pharmaceutical composition of the invention, as defined above. The method of the invention can also be understood as comprising steps (ii)-(iii) carried out on a subject to whom the compound of the invention has been pre-administered. In one embodiment, the pharmaceutical composition is administered in an amount suitable to enhance the contrast in a method of MR imaging (MRI). For further detail on MRI methods the reader is referred to the common general knowledge in the art, e.g. as taught in Chapter 27 "Contrast Agents and Magnetic Resonance Imaging" in "Magnetic Resonance Imaging: Physical and Biological Principles" (4$^{th}$ Edition 2015 Elsevier, Stewart Carlyle Bushong & Geoffrey Clarke, Eds.) or in "Contrast Agents I: Magnetic Resonance Imaging" (2002 Springer-Verlang, Werner Krause, Ed.).

The method of the invention may be used to study a biological marker or process in healthy subjects, or alternatively in subjects known or suspected to have a pathological condition associated with abnormal expression of a biological marker. When the method is used to image a subject known or suspected to have a pathological condition it has utility in a method for the diagnosis of said condition.

The "detection" step of the method of the invention involves detection of signals emitted by the compound of Formula I by means of a detector sensitive to said signals. This detection step can also be understood as the acquisition of signal data.

The "generation" step of the method of the invention is carried out by a computer which applies a reconstruction algorithm to the acquired signal data to yield a dataset. This dataset is then manipulated to generate one or more images and/or one or more spectra showing the location and/or amount of signals.

The "subject" of the invention can be any human or animal subject. In one embodiment, the subject of the invention is a mammal. In one embodiment said subject is an intact mammalian body in vivo. In another embodiment, the subject of the invention is a human.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes a method for the synthesis of an exemplary compound of the invention, Mn Chelate 1.

Example 2 describes a method for the synthesis of a prior art compound, Mn Platform.

Example 3 describes a method that was used for measurement of r1 and r2 relaxivities of a number of Mn chelate compounds.

Example 4 describes a method for assessing trans-metalation with Zn of a number of Mn chelate compounds.

Example 5 describes a method used for preparation of $^{54}$Mn labeled versions of Mn chelate compounds for use in the biodistribution studies of Example 6.

LIST OF ABBREVIATIONS USED IN THE EXAMPLES

AcN acetonitrile
d day(s)
DMSO dimethyl sulfoxide
EtOAc ethyl acetate
ESI electrospray ionization
h hour(s)
LCMS liquid chromatography with mass spectra detection
LOD limit of detection
MTBE methyl tert-butyl ether
MeCN acetonitrile
MeOH methanol
NMR nuclear magnetic resonance
PTFE poly(tetrafluoroethane)
rcf relative centrifugal forc
THF tetrahydrofuran
UPLC ultra performance liquid chromatography
wt % weight percent Example 1

Synthesis of Mn Chelate 1

Example 1(i)

Synthesis of N,N'-((methylazanediyl)bis(ethane-2,1-diyl))bis(4-methylbenzenesulfonamide)

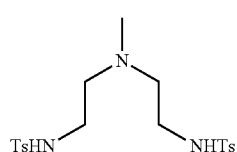

A 1 L round bottomed flask fitted with a magnetic stir bar was charged with N-tosylaziridine (49 g, 248 mmol) and AcN (450 mL). 41% aqueous methylamine (12 mL, 121 mmol) was added and stirred at ambient temperature for 36 h. A second aliquot of N-tosylaziridine (1.7 g, 8.62 mmol) was added and stirred at ambient temperature for an additional 48 h. The solvent was removed in vacuo and the crude residue was recrystallized from EtOH to give 45 g (87%) of the desired product as a white solid. $^1$H NMR (400 MHz, DMSO-D$_6$, δ) 7.68 (4H, m), 7.36 (6H, m), 2.75 (4H, t), 2.38 (6H, s), 2.22 (4H, t), 1.93 (3H, s).

Example 1(ii)

Synthesis of Protected Cyclic 2-Arm Chelate

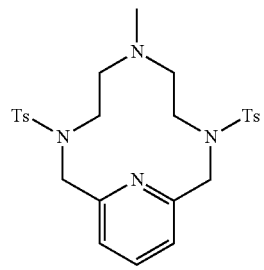 [SMILES: Cc1ccc(S(=O)(=O)N2CCN(C)CCN(S(=O)(=O)c3ccc(C)cc3)Cc3cccc(n3)C2)cc1]

A 12 L 3-necked round bottomed flask fittwith with a reflux condenser and a mechanical stirrer was charged with N,N'—((methylazanediyl)bis(ethane-2,1-diyl))bis(4-methylbenzenesulfonamide (93 g, 218.5 mmol) and AcN (8.3 L). 2,6-bis(chloromethyl)pyridine (38.5 g, 218.5 mmol) was added and the resulting solution was heated at 80° for 16 h. The reaction mixture was cooled to ambient temperature and solvent was removed in vacuo until crystallization began. The resulting crystals were collected via vacuum filtration to afford 86.9 g (75%) of the desired product as a white solid (ESI: m/z=530 (M+H$^+$)).

Example 1(iii)

Synthesis of Deprotected 2-Arm Cyclic Chelate

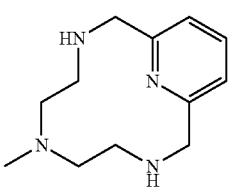 [SMILES: CN1CCNCc2cccc(n2)CNCC1]

A 1 L 3-necked round bottomed flask fitted with a mechanical stirrer was charged with protected cyclic 2-arm chelate (150 g, 284 mmol) and concentrated sulfuric acid (250 mL, 4.69 mol) and heated at 100° C. for 15 h. The solution was poured onto ice and the pH was adjusted to 7.4 with the addition of 50 wt % NaOH in water resulting in the formation of a white solid. AcN (200 mL) was added and the white solid was removed via vacuum filtration. The filtrate was evaporated to dryness to give a brown foam. The foam was dissolved in water (200 mL) and purified with Amberlite A26 resin in its hydroxide form to give 61 g (98%) of the desired product as a tan solid. $^1$H NMR (400 MHz, CD$_3$CN, δ) 7.56 (1H, m), 7.03 (2H, m), 3.76 (4H, s), 2.47 (4H, m), 2.19 (3H, s), 1.95 (4H, s).

Example 1

(iv): Synthesis of Protected 2-Arm C5 Chelate

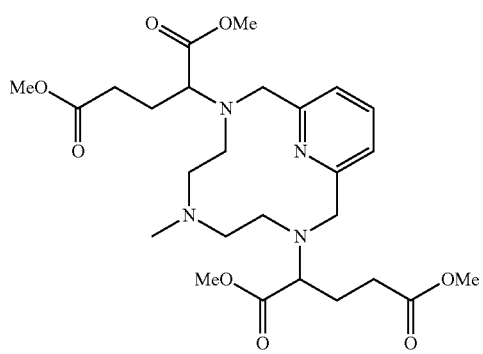 [SMILES: COC(=O)CCC(C(=O)OC)N1CCN(C)CCN(C(CCC(=O)OC)C(=O)OC)Cc2cccc(n2)C1]

A 500 mL round bottomed flask fitted with a magnetic stir bar was charged with deprotected 2-arm cyclic chelate (20.0 g, 90.8 mmol; Example 1(iii)) and AcN (160 mL). Diisopropylethylamine (38.7 mL, 217 mmol) and dimethyl 2-bromopentanedioate (47.7 g, 199.7 mmol) were added and the resulting solution was stirred at 65° C. for 20 h. Diisopropylethylamine (9.75 mL, 54.6 mmol) and dimethyl 2-bromopentanedioate (11.8 g, 49.4 mmol) were added and the resulting solution was stirred at 65° C. for an additional 19 h. The solvent was removed in vacuo to leave a red oil. The oil was then dissolved in water (300 mL) and washed with EtOAc (300 mL). The EtOAc layer was then extracted with water (2×50 mL) and combined with the initial aqueous layer and the water was removed in vacuo to leave a red oil was used without further purification.

Example 1(v)

Synthesis of Mn 2-arm C5 chelate

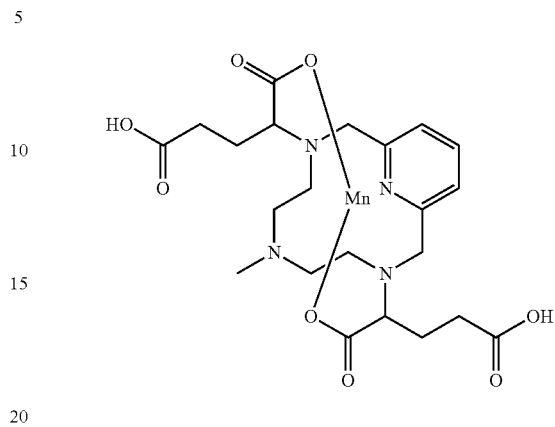

A 1 L round bottomed flask fitted with a magnetic stir bar was charged with protected Mn 2-arm C5 chelate (48.7 g, 90.8 mmol) and water (450 mL). Sodium hydroxide (29.1 g, 726 mmol) was added and stirred at ambient temperature for 2 h. The reaction mixture was washed with EtOAc (250 mL) and the layers were separated. The aqueous layer was washed again with EtOAc (2×100 mL) and the aqueous layer was collected. Manganese chloride tetrahydrate (19.6 g, 99 mmol) was added to the aqueous solution. The pH was adjusted to 7.1 with 6 M NaOH and stirred at ambient temperature for 17 h and then at 90° C. for 2.5 h. After cooling to ambient temperature, the pH was adjusted to 10.1 with 50 wt % aqueous NaOH and a fine brown precipitate formed. The precipitate was removed via centrifugation at 3000 rcf for 20 min and the supernatant was collected and evaporated to dryness in vacuo. The residue was triturated with MeOH (127 mL) at 40° C. for 1.5 h. The insoluble white solid was removed via centrifugation at 3000 rcf for 30 min. The supernatant was evaporated to dryness in vacuo to give an off-white solid which was purified on $C_{18}$ silica gel (3% AcN in water) to give 36.8 g (75%) of the desired product as an off white solid (ESI: m/z=534 (M+H$^+$)).

Example 1(vi)

Synthesis of Mn Chelate 1

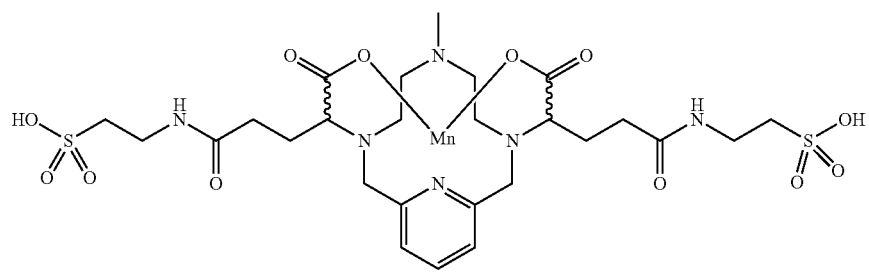

A 25 mL 2-necked round bottomed flask fitted with a magnetic stir bar was charged with taurine (0.217 g, 1.76 mmol) and water (8.7 mL). The pH of the resulting solution was adjusted to 7 using 1.0 M aqueous sodium hydroxide solution. Subsequently, Mn 2-arm C5 chelate (0.503 g, 0.83 mmol) was added followed by EDCI—HCl (0.374 g, 80.98 mmol) and HOBt hydrate (0.05 g, 0.35 mmol). The pH was maintained at 6 with addition of 1.0 M HCl or 1.0 M NaOH as needed while stirring at ambient temperature for 18 h. The reaction solution was evaporated to dryness in vacuo and the crude product was purified on 018 silica gel 5% AcN in water to 20% AcN in water) to give 0.33 g (53%) of the desired product as a colorless glass (ESI: m/z=748 (M+H$^+$)).

Example 2

Synthesis of Mn Chelate 2

Example 2(i): Synthesis of Methyl-2-bromo-6—(2, 2,2-trifluoroacetamido)hexanoate

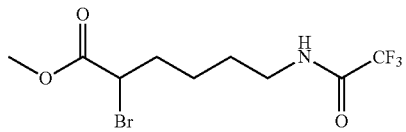 [SMILES: COC(=O)C(Br)CCCCNC(=O)C(F)(F)F]

N-ε-trifluoroacetamido-L-lysine (25 g) and sodium bromide (37.2 g) were added to a 3-necked jacketed reaction vessel fitted with an internal thermocouple, mechanical stirrer, and a powder funnel. The solids were subsequently dissolved in water (69 mL) and aqueous HBr solution (20.9 mL, 8.9 M). The powder funnel was removed and an addition funnel charged with sodium nitrite (12.8 g) that had been dissolved in 16.5 mL of water. The addition funnel was fitted with a nitrogen inlet was added to the reaction vessel. The reaction exhaust was passed through a solution of sodium sulfite prior to being vented into the fume hood. The reaction mixture was chilled to <0° C. and then the sodium nitrite solution was slowly added to the reaction mixture at such a rate that the internal reaction temperature was not allowed to exceed 3° C. The addition funnel was removed, and a separate addition funnel preloaded with concentrated sulfuric acid (5.5 mL) was fitted to the reaction vessel. The sulfuric acid was added to the reaction mixture at such a rate that the internal reaction temperature did not exceed 5° C. Following this addition, the reaction mixture was actively sparged with N$_2$ to remove dissolved Br$_2$. After sparging for 20 minutes at room temperature, sparging was discontinued, and the reaction mixture was partitioned against 80 mL of methyl-tert-butyl ether (MTBE). The mixture was rapidly stirred for five minutes, and then the phases were allowed to separate. The organic layer was collected, and the aqueous layer was extracted with two additional 70 mL portions of MTBE. The combined organic layers were washed with several portions of 5% Na$_2$SO$_3$ solution until nearly colorless, and then subsequently washed with brine (100 mL), dried (MgSO$_4$), filtered and concentrated under reduced pressure to provide a pale yellow colored oil which was further dried under high vacuum overnight. The dried material was dissolved in methanol (350 mL) and p-TsOH monohydrate (0.35 g) was added. The mixture was heated at 65° C. under nitrogen, overnight. Following this time, heating was discontinued and the reaction mixture was allowed to cool to room temperature. The reaction mixture was concentrated under reduced pressure to provide a yellow oil that was subsequently purified by flash chromatography on SiO$_2$ (330 g column, 5→50% EtOAc-hexanes over 12 column volumes). The isolated product was a nearly colorless oil 20.3 g, (62%). LCMS: t$_r$=3.72 min., (M–H)$^-$ 318, 320 (Column: Waters Aquity UPLC BEH Shield RP18 1.7 μm 2.1×75 mm; Channel A: 0.1% formic acid in water; Channel B: 0.1% formic acid in MeCN; Flow: 1.0 mL/min.; Program: 0.0-0.5 min., 98:2 A:B; 0.5-9.0 min. 98:2 A:B→2: 98 A:B; 9.0-9.5 min., 2:98 A:B; Gradient: linear)

Example 2(ii)

Bis-[4, 10]-(2-(methyl-6-(2,2,2-trifluoroacetamido) hexanoate))-pyramine

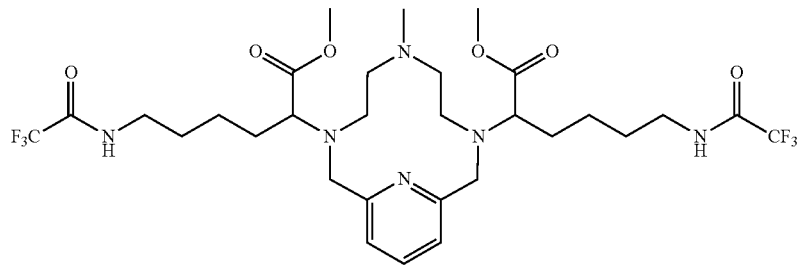 [SMILES: COC(=O)C(CCCCNC(=O)C(F)(F)F)N1CCN(C)CCN(C(CCCCNC(=O)C(F)(F)F)C(=O)OC)Cc2cccc(n2)C1]

To a flask containing the deprotected 2-arm cyclic chelate (1.83 g; Example 1(iii)) was added anhydrous MeCN (17.1 mL), followed by diisopropylethylamine (3.6 mL), and subsequently methyl-2-bromo-6-(2,2,2-trifluoroacetamido) hexanoate (5.87 g). The reaction vessel was placed in an oil bath maintained at 65° C. for 18 h. Following this time, an additional quantity of diisopropylethylamine (1.5 mL) and methyl-2-bromo-6—(2,2,2-trifluoroacetamido)hexanoate (2.95 g) dissolved in 3 mL of MeCN was added to the reaction mixture. The reaction mixture was allowed to continue stirring in a 65° C. oil bath for an additional 18 h. Following this time, the reaction mixture was concentrated under reduced pressure and the resulting residue was taken up in EtOAc (40 mL) and washed with brine (30 mL). The aqueous washing was back extracted with two additional 20 mL portions of EtOAc and the combined organic extracts were dried (Na$_2$SO$_4$), filtered, and concentrated under reduced pressure. The residue was dissolved in water (24 mL) with gentle heating (65° C. water bath). The mixture was removed from the water bath, allowed to briefly cool, and then diethylether (10 mL) was added to the mixture. The mixture was vigorously shaken, and was subsequently transferred to a separatory funnel. The phases were separated, and the aqueous layer was extracted with two additional 5 mL portions of diethylether. Subsequently, saturated sodium chloride solution (24 mL) was added to the aqueous layer and the aqueous layer was subsequently extracted with three portions of EtOAc (15 mL each). The combined EtOAc extracts were dried (Na$_2$SO$_4$), filtered, and concentrated under reduced pressure to provide the product as an oil 5.75 g (98%). LCMS: t$_r$=6.84 min., (M+H)$^+$=699 (Column: Waters XBridge Shield RP18 2.5 μm 4.6×50 mm; Channel A: 0.1% formic acid in water; Channel B: 0.1% formic acid in MeCN; Flow: 1.0 mL/min.; Program: 0.0-1.0 min., 98:2 A:B; 1.0-12.0 min. 98:2 A:B→0:100 A:B; 12.0-16.0 min., 0:100 A:B; Gradient: linear)

Example 2(iii)

Synthesis of Bis-[4,10]-(2-(6-ammonium-potassiumhexanoate))-pyramine bistrifluoroacetate

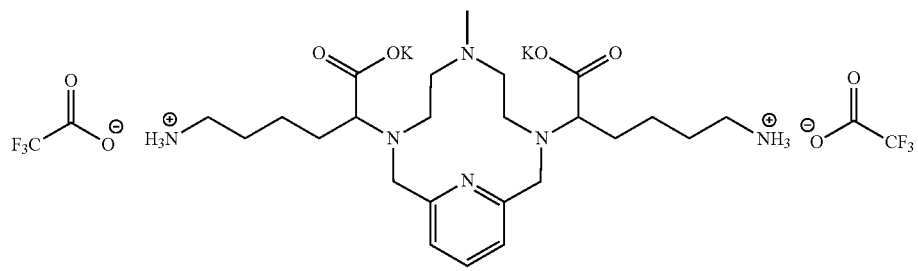

The starting material Bis-[4, 10]-(2-methyl-6-(2,2,2-trifluoroacetamido)hexanoate))-pyramine (8.9 g) was added to a 2 mmol/g solution of aqueous KOH (27.1 g) and allowed to stir in a 40° C. water bath for 1 h. Following this time, methanol (10 mL) was added to the reaction mixture to assist solubilization, the reaction mixture was allowed to continue stirring at room temperature overnight. The pH of the reaction mixture was adjusted to 7 with 6 M HCl, and the solvent was removed under reduced pressure providing a caramel colored semisolid. The residue was coevaporated with two 50 mL portions of 2-propanol, and was subsequently triturated with methanol (25 mL), filtered, and the solids were washed with two additional 5 mL portions of methanol. The filtrate was concentrated under reduced pressure and the residue was further dried under high vacuum to provide a peach colored foam 9.3 g (93%) LCMS: t$_r$=4.99 min., (M+H)+=479; (M−H)−477 (Column: Agilent Zorbax SB-Aq, 3×100 mm, 3.5 μm; Channel A: 10 mM ammonium formate in water (pH 6.4); Channel B: MeCN; Flow: 1.0 mL/min.; Program: 0.0-10.0 min. 100:0 A:B→70:30 A:B; 10.0-10.5 min. 70:30 A:B→0:100 A:B; 10.5-15.0 min. 0:100 A:B; Gradient: linear).

Example 2(iv)

Synthesis of (2R,3R)-2,3-diacetoxy-4-morpholino-4-oxobutanoic acid

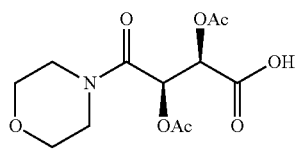

(+)-diacetyl-L-tartaric anhydride (2.0 g) was dissolved in EtOAc (46 mL) and morpholine (X) (0.80 mL) was added. The mixture was sealed and allowed to stir at room temperature for 18 h. The reaction mixture was concentrated under reduced pressure to provide a nearly colorless foam that was further dried under high vacuum. The reaction yielded 2.85 g (quant.) LCMS: t$_r$=1.55 min., (M+H)+=304 (Column: Agilent Zorbax SB-Aq, 3×100 mm, 3.5 μm; Channel A: 10 mM ammonium formate in water (pH 6.4); Channel B: MeCN; Flow: 1.0 mL/min.; Program: 0.0-10.0 min. 100:0 A:B→70:30 A:B; 10.0-10.5 min. 70:30 A:B→0:100 A:B; 10.5-15.0 min. 0:100 A:B; Gradient: linear).

Example 2(v)

Synthesis of (2R,3R)-1-((2,5-dioxopyrrolidin-1-yl)oxy)-4-morpholino-1,4-dioxobutane-2,3-diyl diacetate

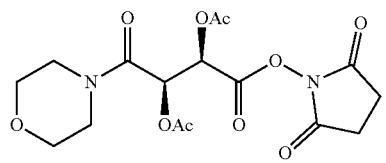 [SMILES: CC(=O)O[C@@H](C(=O)ON1C(=O)CCC1=O)[C@@H](OC(C)=O)C(=O)N1CCOCC1]

To a solution of (2R,3R)-2,3-diacetoxy-4-morpholino-4-oxobutanoic acid (6.93 g) in EtoAc (80 mL) was added N-hydroxysuccinimide (2.30 g). The resulting solution was cooled to between 0-5° C. Dicyclohexylcarbodiimide (4.72 g) was added to the reaction mixture in one portion followed by an additional 11 mL of EtOAc. The reaction mixture was allowed to warm to room temperature overnight. Over this time the reaction had gone from a homogeneous, pale yellow solution to a colorless thick suspension. The reaction mixture was diluted with EtOAc (100 mL) and the thick mixture was agitated in a 40° C. water bath for 1 h. Following this time, the warm suspension was filtered through a 0.45 µm PTFE filter and the solids were washed with several portions of EtOAc. The solids were collected, suspended in EtOAc (400 mL) and heated in a 50° C. water bath for 2 h. The mixture was once again filtered through a 0.45 µm PTFE filter and the solids were washed with several portions of EtOAc. The colorless filtrate was concentrated under reduced pressure to provide the desired product: 5.49 g (60%) 1H NMR (CDCl3) δ 6.00 (d. J=3.0 Hz, 1H), δ 5.92 (d. J=3.1 Hz, 1H), b 3.81-3.47 (m., 8H), b 2.85 (s., 4H), b 2.22 (s., 3H), δ 2.20 (s., 3H).

Example 2(vi)

Synthesis of Chelate 2

(2R,3R)-1-((2,5-dioxopyrrolidin-1-yl)oxy)-4-morpholino-1,4-dioxobutane-2,3-diyl diacetate was suspended in 70 mL of MeCN at 40° C. and the mixture was agitated in an effort to dissolve (2R,3R)-1-((2,5-dioxopyrrolidin-1-yl)oxy)-4-morpholino-1,4-dioxobutane-2,3-diyldiacetate (It took nearly 60 min. for near complete dissolution of (2R,3R)-1-((2,5-dioxopyrrolidin-1-yl)oxy)-4-morpholino-1,4-dioxobutane-2,3-diyldiacetate). In a separate vessel, a solution of deprotected 2-arm cyclic chelate (4.4 g; Example 1(iii)) in 75 mL of water was prepared, and to this solution was added 2.87 g of solid potassium bicarbonate. The pH of the mixture was 8.0. The solution of (2R,3R)-1-((2,5-dioxopyrrolidin-1-yl)oxy)-4-morpholino-1,4-dioxobutane-2,3-diyldiacetate in MeCN was transferred to an addition funnel and was slowly added to the aqueous mixture containing deprotected 2-arm cyclic chelate. The temperature of the reaction mixture was maintained through the use of a room temperature water bath. Following the addition of most of X the pH of the reaction mixture was 7.4. Any remaining undissolved X was suspended in MeCN and was added directly to the reaction mixture. After stirring for two hours, the pH of the reaction mixture was stable at 7.8, the reaction mixture was allowed to continue stirring at room temperature for 72 h. Following the allotted time, the reaction mixture was concentrated under reduced pressure to provide 12.1 g of crude residue. The residue was taken up in 1:1 methanol-water (100 mL). To the mixture we added potassium carbonate (7.94 g) at room temperature. The pH of the mixture following this addition was 12.2. The reaction mixture was allowed to continue stirring at room temperature for 18 h. Following this time, the reaction mixture was concentrated under reduced pressure. We added methanol (50 mL) to the resulting residue and the suspension was agitated for several minutes before being filtered through a 0.45 µm PTFE filter. The collected solids were washed with three, 10 mL portions of methanol and then the combined methanol filtrate was concentrated under reduced pressure and the resulting residue was placed under high vacuum for 16 h. The isolated residue was suspended in 20 mL of 1:1 MeCN—H2O, filtered, and the filtrate was iteratively purified in 6 mL portions by reversed phase chromatography on RediSep Rf Gold C18Aq. (275 g column, 100% water over 2 column volumes). Two peaks eluted from the column (265 nm), the later eluting peak was collected and concentrated to provide the desired product as a yellow solid: 5.06 g (70%) LCMS: t,=2.43 min. (M+H)+=743; (M–H)–741 (Column: Waters Aquity UPLC BEH Shield RP18 1.7 µm 2.1×75 mm; Channel A: 0.1% formic acid in water; Channel B: 0.1% formic acid in MeCN; Flow: 0.8 mL/min.; Program: 0.0-0.5 min., 98:2 A:B; 0.5-9.0 min. 98:2 A:B→2:98 A:B; Gradient: linear).

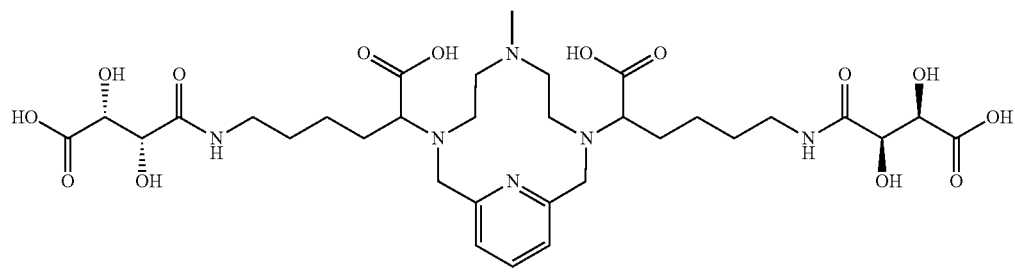 [SMILES: CN1CCN(C(CCCCNC(=O)[C@H](O)[C@@H](O)C(=O)O)C(=O)O)Cc2cccc(n2)CN(C(CCCCNC(=O)[C@H](O)[C@@H](O)C(=O)O)C(=O)O)CC1]

Example 2(vii)

Alternative Synthesis of Chelate 2

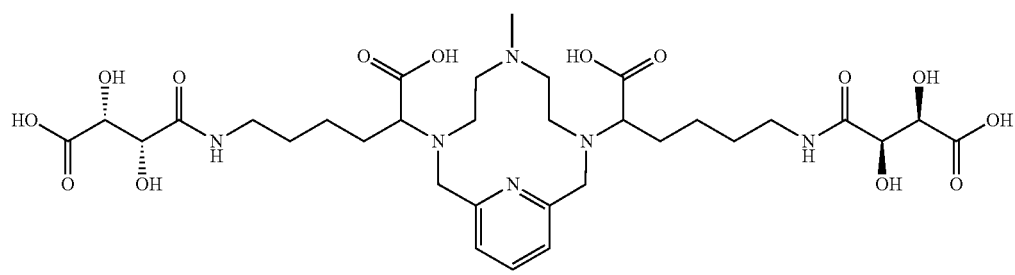 [SMILES: CN1CCN(C(CCCCNC(=O)[C@H](O)[C@@H](O)C(=O)O)C(=O)O)Cc2cccc(n2)CN(C(CCCCNC(=O)[C@H](O)[C@@H](O)C(=O)O)C(=O)O)CC1]

The starting material bis-[4, 10]-(2-(6-ammonium-potassiumhexanoate))-pyramine bistrifluoroacetate (1.0 g) is dissolved in glacial acetic acid (5 mL). Solid (3R,4R)-2,5-dioxotetrahydrofuran-3,4-diyl diacetate (1.0 g) is added and the mixture is allowed to stir at 40° C. for 18 h. Following the allotted time the acetic acid is removed under reduced pressure and by coevaporation with toluene (3×50 mL). The resulting residue is dissolved in 10 mL of 1:1 MeOH—H$_2$O and potassium hydroxide (1.4 g) is added. The progress of the hydrolysis reaction is monitored by HPLC-MS and additional KOH is added as needed. Upon completion, the reaction is neutralized to pH 7.0 with aqueous HCl and the solvent is removed under reduced pressure. The resulting residue is triturated with methanol (3×1 mL) and filtered. The filtrate is concentrated under reduced pressure and purification is achieved as needed by reverse phase C$_{18}$ chromatography.

Example 2(viii)

Synthesis of Mn Chelate 2

The starting material Chelate 2 (2.98 g) was dissolved in water 16 mL. The pH of the solution was adjusted to 8.2 by carefully adding concentrated HCl. At this time, MnCl2.4 H$_2$O (1.19 g) was added to the reaction mixture and the pH of the mixture fell to 3.4. The pH of the reaction mixture was adjusted to 6.5 through the addition of 2.7 M aqueous KOH solution. The reaction mixture was allowed to stir for 3 h. at room temperature. Following this time the pH of the reaction mixture was adjusted to 10 by the addition of 2.7 M aqueous KOH solution. The brown mixture was stirred for 1 h, and then the entire mixture was filtered through a 0.45 μm PTFE filter. The filtrate was concentrated under reduced pressure and further dried under high vacuum for 18 h. The residue was dissolved in 10 mL of water and was iteratively purified in two batches by reversed phase chromatography on RediSep Rf Gold C18Aq. (275 g column; 100% water over 2 column volumes, then 0%→5% MeCN-water over 2 column volumes, then hold at 5% MeCN-water for 2 column volumes). The desired product eluted between 4 and 5 column volumes. Fractions containing the desired product were collected and concentrated and were further dried under high vacuum. The product was a light yellow solid: 1.39 g (43%) LCMS: t$_r$=2.87 min. (M+H)+=796; (M−H)− 794 (Column: Waters Aquity UPLC BEH Phenyl 1.7 μm 2.1×75 mm; Channel A: 25 mM aqueous ammonium acetate; Channel B: MeCN; Flow: 1.0 mL/min.; Program: 0.0-5.0 min., 95:5 A:B 80:20 A:B; 5.0-10.0 min., 20:80 A:B→5:95 A:B; 10.0-11.0 min 5:95 A:B; Gradient: linear).

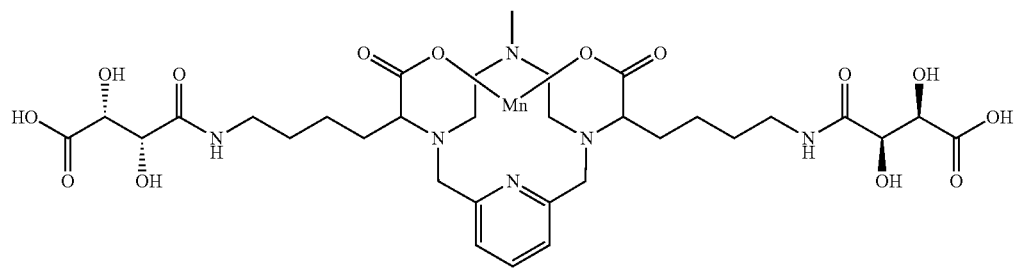

Example 3

Mn Platform

Example 3(i)

Synthesis of N,N'—((methylazanediyl)bis(ethane-2,1-diyl))bis(4-methylbenzenesulfonamide)

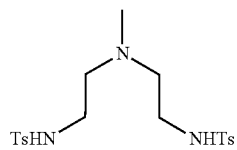

A 1 L round bottomed flask fitted with a magnetic stir bar was charged with N-tosylaziridine (49 g, 248 mmol) and AcN (450 mL). 41% aqueous methylamine (12 mL, 121 mmol) was added and stirred at ambient temperature for 36 h. A second aliquot of N-tosylaziridine (1.7 g, 8.62 mmol) was added and stirred at ambient temperature for an additional 48 h. The solvent was removed in vacuo and the crude residue was recrystallized from EtOH to give 45 g (87%) of the desired product as a white solid. $^1$H NMR (400 MHz, DMSO-D$_6$, δ) 7.68 (4H, m), 7.36 (6H, m), 2.75 (4H, t), 2.38 (6H, s), 2.22 (4H, t), 1.93 (3H, s).

Example 3(ii)

Synthesis of Protected Cyclic 2-Arm Chelate

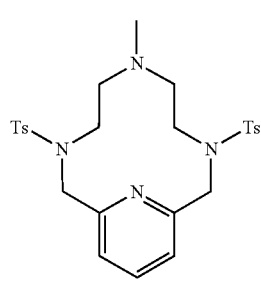 [SMILES: Cc1ccc(S(=O)(=O)N2CCN(C)CCN(S(=O)(=O)c3ccc(C)cc3)Cc3cccc(n3)C2)cc1]

A 12 L 3-necked round bottomed flask fitted with a reflux condenser and a mechanical stirrer was charged with N,N'—((methylazanediyl)bis(ethane-2,1-diyl))bis(4-methylbenzenesulfonamide (93 g, 218.5 mmol) and AcN (8.3 L). 2,6-bis(chloromethyl)pyridine (38.5 g, 218.5 mmol) was added and the resulting solution was heated at 80° for 16 h. The reaction mixture was cooled to ambient temperature and solvent was removed in vacuo until crystallization began. The resulting crystals were collected via vacuum filtration to afford 86.9 g (75%) of the desired product as a white solid (ESI: m/z=530 (M+H$^+$)).

Example 3(iii)

Synthesis of Protected Mn 0-Arm Chelate

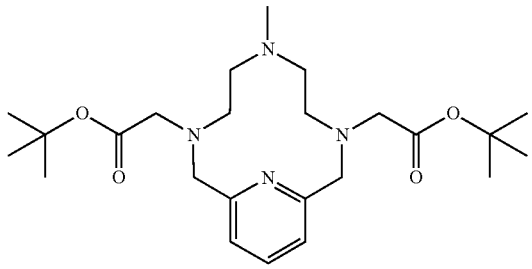 [SMILES: CN1CCN(CC(=O)OC(C)(C)C)Cc2cccc(n2)CN(CC(=O)OC(C)(C)C)CC1]

A 100 mL 3-necked round bottomed flask fitted with a magnetic stir bar and a reflux condenser was charged with protected cyclic 2-arm chelate (4.51 g, 8.53 mmol) and concentrated sulfuric acid (18.0 mL) and heated at 100° C. for 18 h. The reaction was cooled to ambient temperature and placed in an ice bath prior to adjusting the pH to 9.9 with 50% aqueous NaOH. The resulting suspension was transferred to a 250 mL 3-necked round bottomed flask and anhydrous potassium carbonate (11.78 g, 85.2 mmol) was added followed by AcN (25 mL) and t-butylbromoacetate (6.64 g, 34.0 mmol) and the reaction was heated at 70° C. for 3 h. The reaction was cooled to ambient temperature and the solids were removed via vacuum filtration. The filtrate was extracted with AcN (3×50 mL) and the organic layer was evaporated to dryness to give a dark brown oil which was purified on C$_{18}$ silica gel (100% water to 100% AcN in water) to give 1.28 g (33%) of the desired product as an off white solid. $^1$H NMR (400 MHz, CD$_3$CN, δ) 7.67 (1H, m), 7.12 (2H, m), 5.14 (2H, bs), 3.95 (4H, m), 3.44 (4H, m), 3.28 (6H, m), 3.16 (2H, m), 2.78 (3H, s), 1.42 (18H, s).

Example 3(iv)

Synthesis of Deprotected Mn 0-Arm Chelate

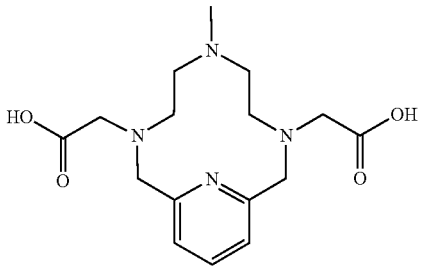 [SMILES: CN1CCN(CC(=O)O)Cc2cccc(n2)CN(CC(=O)O)CC1]

A 3-necked 100 mL round bottomed flask fitted with a magnetic stir bar and a reflux condenser was charged with protected Mn 0-arm chelate (1.28 g, 2.85 mmol), AcN (8.4 mL) and THF (21 mL). 88% aqueous formic acid (29.1 mL, 556 mmol) was added and the resulting solution was heated at 65° C. for 4 h. A second aliquot of 88% aqueous formic acid (29.1 mL, 556 mmol) was added and heating was continued for an additional 9 h. The solvent was removed in vacuo to leave a yellow oil which was used without further purification. ¹H NMR (400 MHz, CD₃OD, δ) 7.74 (1H, m), 7.20 (2H, m), 4.07 (4H, m), 3.65 (4H, m), 2.91 (3H, s), 2.99 (4H, m), 1.92 (4H, m).

Example 3(v)

Synthesis of Mn Platform

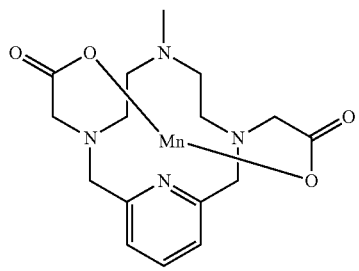

A 250 mL round bottomed flask fitted with a magnetic stir bar was charged with deprotected Mn 0-arm chelate (0.959 g, 2.85 mmol) and manganese(II) chloride tetrahydrate (1.119 g, 5.65 mmol). The pH was adjusted to 7.4 with 1.0 M NaOH and 1.0 M HCl as needed and the resulting solution was stirred at ambient temperature for 15.5 h. The pH was then adjusted to 10 with saturated aqueous sodium carbonate and the resulting off-white precipitate was removed via vacuum filtration. The filtrate was concentrated to dryness in vacuo and purified on $C_{18}$ silica gel (100% water to 10% AcN in water) to give 0.511 g (46% over 2 steps) of the desired product as a pale yellow solid (ESI: m/z=390 (M⁺)).

Example 4

General Method for Measurement of r1 and r2 Relaxivities

Manganese containing chelates were dissolved in water at concentrations ranging from 5 to 0 mM Mn. T1 and T2 relaxation times were then measured at 60 MHz and 40° C. using a Bruker mq60 relaxometer. Linear fits ($R^2$>0.99 in all cases) of 1/T1 or 1/T2 as a function of Mn concentration gave r1 or r2 values respectively.

TABLE 1 r1 and r2 relaxivities in water at 60 MHz and 40° C.

| Compound | r1 (mM⁻¹s⁻¹) | r2 (mM⁻¹s⁻¹) |
| --- | --- | --- |
| Mn Platform | 1.7 | 4.7 |
| Mn Chelate 1 | 3.4 | 10.7 |
| Mn Chelate 2 | 4.6 | 12.6 |

The values in Table 1 are relaxivities in water. The r1 value represents the ability of the chelate to generate T1 (or positive) contrast in a MR scanner while the r2 value represents the ability of the chelate to generate T2 (or negative) contrast in a MR scanner.

Example 5

Method for Assessing Trans-Metalation with Zn

Figure 2:
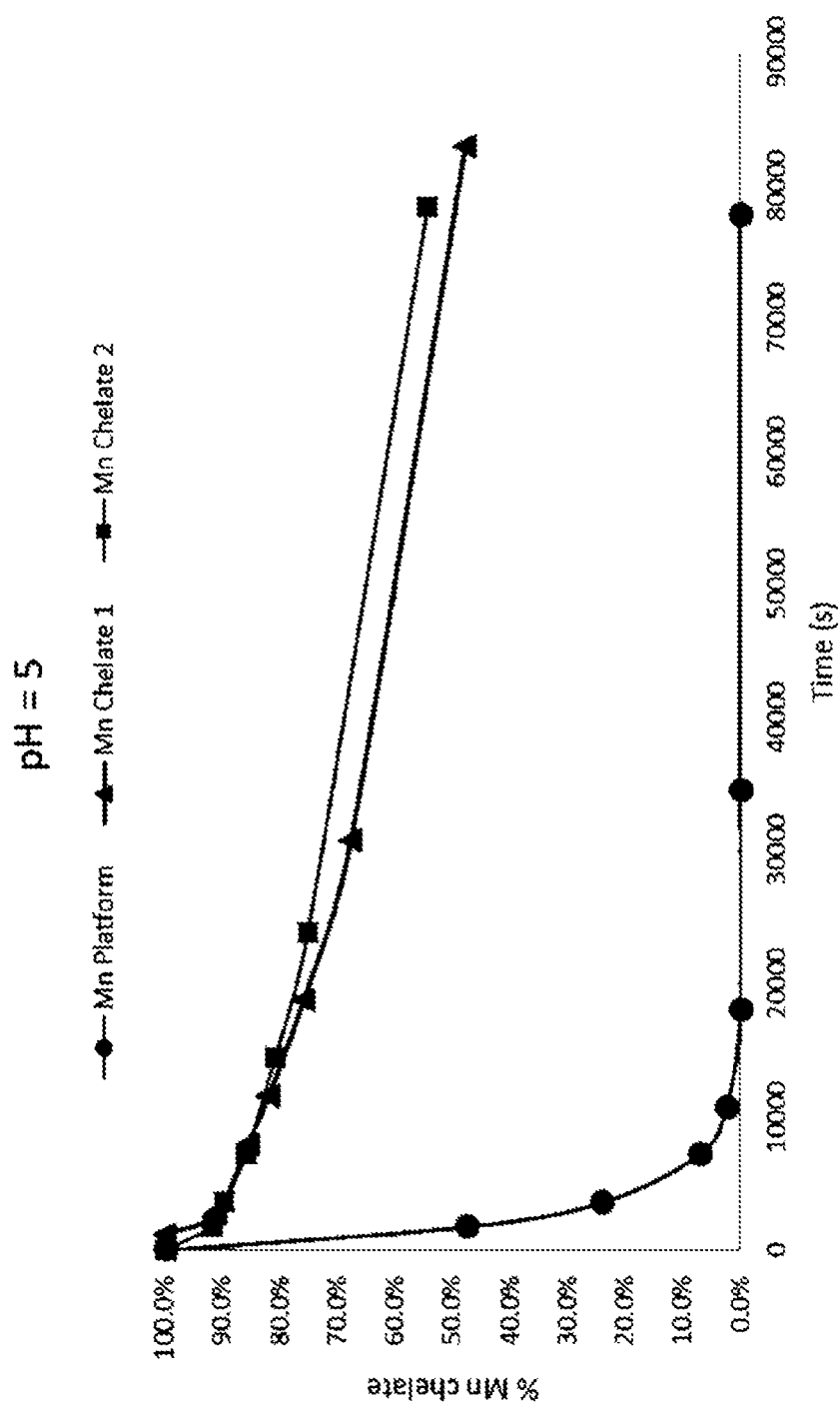
FIG. 2 shows (circles=Mn Platform, triangles=Mn Chelate 1 and squares=Mn Chelate 2) % Mn chelate as a function of time at pH=5 and 40° C. in the presence of 100 fold excess ZnCl$_2$.

Mn chelates were dissolved in aqueous solutions containing 200 mM ZnCl₂ and 15 mM ammonium formate at either pH=4 (FIG. 1) or 5 (FIG. 2). The resulting solutions were incubated at 40° C. with mixing and aliquots were periodically analyzed by HPLC-MS. The Mn and Zn containing chelates were identified by MS and percent Mn containing chelate remaining in the solution as measured by integration at 265 nm were plotted as a function of time.

Slower trans-metalation with Zn (higher % Mn chelate as a function of time) was interpreted as a more stable chelate.

The invention claimed is:

1. A compound of Formula I or a salt or solvate thereof:

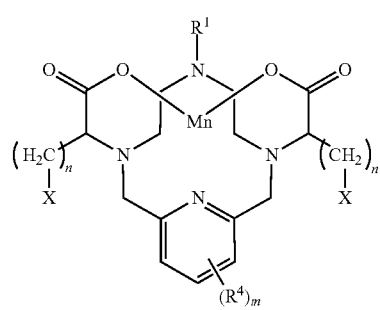

(I)

wherein:

n is an integer of 1 to 4

$R^1$ is $C_{1-3}$ alkyl or —(CH₂)$_{n+1}$—C(=O)—NR²R³;

each X is —C(=O)—NR²R³ or —NH—C(=O)—R³;

each $R^2$ is hydrogen, $C_{1-4}$ alkyl or an anionic substituent;

each $R^3$ is an anionic substituent optionally linked via a $C_{1-4}$ alkylene; and, $R^4$ is independently selected from the group comprising hydroxy, halo, amino, amido, $C_{1-6}$ alkyl and $C_{1-6}$ hydroxyalkyl and m is between 0-3, wherein each anionic substituent is independently selected from phosphate, phosphonate, hydroxycarboxylate, tetrazole, thiazolidindione, nitromethylsulfonylphenyl, 4-nitrothiophenol, nitromethylcarboxyphenyl, 2,4-dinitrophenol, or malonitrile.

2. The compound as defined in claim 1 wherein $R^1$ is $C_{1-3}$ alkyl.

3. The compound as defined in claim 1 wherein $R^1$ is —(CH₂)$_{n-1}$—C(=O)—NR²R³.

4. The compound as defined in claim 1 wherein n is 4.

5. The compound as defined in claim 1 wherein each X is —C(=O)—NR²R³.

6. The compound as defined in claim 1 wherein each X is —NH—C(=O)—R³.

7. The compound as defined in claim 1 wherein m is 0.

8. The compound as defined in claim 1 wherein each anionic substituent has a pKa less than physiological pH.

9. The compound as defined in claim 1 wherein each of said anionic substituents is over 90% anionic at physiological pH.

10. The compound as defined in claim 1 which is selected from the following compounds:

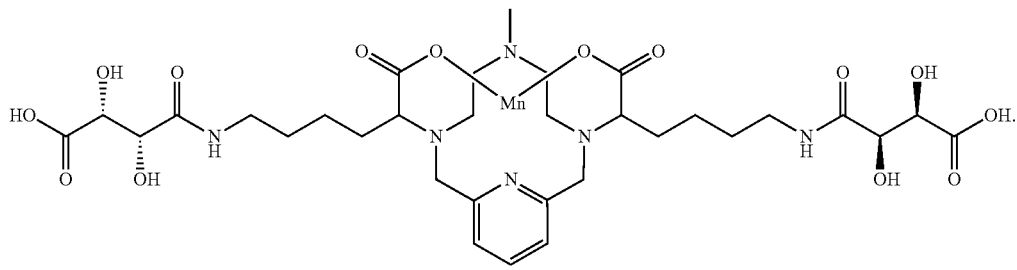

11. A pharmaceutical composition comprising the compound of Formula I as defined in claim 1 together with a biocompatible carrier in a form suitable for mammalian administration.

12. A method comprising:
   (i) administration to a subject of the compound of Formula I as defined in claim 1;
   (ii) detection of magnetic resonance (MR) signals from said subject or part of said subject in which said compound has distributed;
   (iii) generation of MR images and/or MR spectra from said detected signals.

13. A method to produce a compound of Formula I as defined in claim 1 comprising reaction of a compound of Formula II:

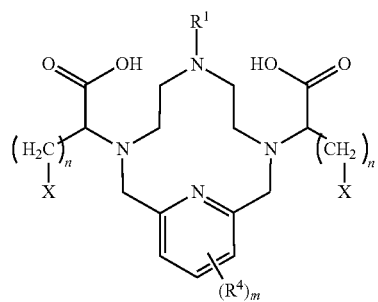

with a suitable source of manganese.

14. The method as defined in claim 13 wherein said suitable source of manganese is manganese(II) chloride.

* * * * *

UNITED STATES PATENT AND TRADEMARK OFFICE
CERTIFICATE OF CORRECTION

Page 1 of 1

PATENT NO. : 11,110,186 B2
APPLICATION NO. : 16/956995
DATED : September 7, 2021
INVENTOR(S) : Brian Christopher Bales, Michael James Rishel and Andreas Richard Meijer It is certified that error appears in the above-identified patent and that said Letters Patent is hereby corrected as shown below:

On the Title Page

Item (72), please add Andreas Richard Meijer, Oslo (NO).

Signed and Sealed this
Twenty-second Day of July, 2025

Coke Morgan Stewart
*Acting Director of the United States Patent and Trademark Office*